United States Patent
Kaynan et al.

(10) Patent No.: US 11,583,675 B2
(45) Date of Patent: Feb. 21, 2023

(54) INHIBITING VIRAL INFECTION USING ALTERNATING ELECTRIC FIELDS

(71) Applicant: Novocure GmbH, Root (CH)

(72) Inventors: Noa Kaynan, Kibbutz Barkai (IL); Tali Voloshin-Sela, Kibbutz Gvat (IL); Moshe Giladi, Moshav Herut (IL); Eilon Kirson, Ramat Hasharon (IL)

(73) Assignee: NOVOCURE GMBH

( * ) Notice: Subject to any disclaimer, the term of this patent is extended or adjusted under 35 U.S.C. 154(b) by 12 days.

(21) Appl. No.: 16/506,633

(22) Filed: Jul. 9, 2019

(65) Prior Publication Data

US 2020/0016399 A1 Jan. 16, 2020

Related U.S. Application Data

(60) Provisional application No. 62/695,925, filed on Jul. 10, 2018.

(51) Int. Cl.
*A61N 1/32* (2006.01)
*A61M 37/00* (2006.01)

(52) U.S. Cl.
CPC ............... *A61N 1/32* (2013.01); *A61M 37/00* (2013.01); *A61M 2205/054* (2013.01)

(58) Field of Classification Search
CPC ..... A61N 1/32; A61N 1/40; A61M 2205/054; A61B 2018/147
See application file for complete search history.

(56) References Cited

U.S. PATENT DOCUMENTS

| | | |
|---|---|---|
| 5,983,130 A | 11/1999 | Phipps |
| 6,868,289 B2 | 3/2005 | Palti |
| 7,016,725 B2 | 3/2006 | Palti |
| 7,089,054 B2 | 8/2006 | Palti |
| 7,136,699 B2 | 11/2006 | Palti |
| 7,146,210 B2 | 12/2006 | Palti |
| 7,333,852 B2 | 2/2008 | Palti |
| 7,467,011 B2 | 12/2008 | Palti |
| 7,519,420 B2 | 4/2009 | Palti |
| 7,565,205 B2 | 7/2009 | Palti |
| 7,565,206 B2 | 7/2009 | Palti |
| 7,599,745 B2 | 10/2009 | Palti |

(Continued)

OTHER PUBLICATIONS

Liao, John B. "Viruses and human cancer." The Yale journal of biology and medicine vol. 79,3-4 (2006): 115-22. (Year: 2006).*

(Continued)

*Primary Examiner* — Carl H Layno
*Assistant Examiner* — Aya Ziad Bakkar
(74) *Attorney, Agent, or Firm* — Ballard Spahr LLP

(57) ABSTRACT

Viral infections in a target region can be inhibited by imposing an alternating electric field in the target region for a duration of time. The alternating electric field has a frequency and a field strength such that when the alternating electric field is imposed in the target region for the duration of time, the alternating electric field inhibits infection of the cells in the target region by the virus. Optionally, the inhibition of viral infections using the alternating electric field approach can be combined with delivering an antiviral agent to the target region so that a therapeutically effective dose of the antiviral agent is present in the target region while the alternating electric fields are imposed.

16 Claims, 4 Drawing Sheets

(56) References Cited

U.S. PATENT DOCUMENTS

| | | |
|---|---|---|
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,440,068 B2 | 9/2016 | Palti et al. |
| 9,504,824 B2 * | 11/2016 | Esenaliev ............ A61M 31/00 |
| 9,655,669 B2 | 5/2017 | Palti et al. |
| 9,750,934 B2 | 9/2017 | Palti et al. |
| 9,910,453 B2 | 3/2018 | Wasserman et al. |
| 10,188,851 B2 | 1/2019 | Wenger et al. |
| 10,441,776 B2 | 10/2019 | Kirson et al. |
| 2006/0167499 A1 | 7/2006 | Palti |
| 2007/0225766 A1 | 9/2007 | Palti |
| 2007/0239213 A1 | 10/2007 | Palti |
| 2008/0146918 A1 | 7/2008 | Magnin |
| 2008/0190886 A1 | 8/2008 | Choi |
| 2012/0029419 A1 | 2/2012 | Palti |
| 2012/0283726 A1 | 11/2012 | Palti |
| 2017/0120041 A1 | 5/2017 | Wenger et al. |
| 2017/0128127 A1 * | 5/2017 | Skalnyi ............. A61B 18/1485 |
| 2017/0215939 A1 | 8/2017 | Palti et al. |
| 2017/0266283 A1 * | 9/2017 | Soikum ................. A61P 35/00 |
| 2017/0281934 A1 * | 10/2017 | Giladi ..................... A61N 1/40 |
| 2018/0001075 A1 | 1/2018 | Kirson et al. |
| 2018/0008708 A1 | 1/2018 | Giladi et al. |
| 2018/0050200 A1 | 2/2018 | Wasserman et al. |
| 2018/0160933 A1 | 6/2018 | Urman et al. |
| 2018/0202991 A1 | 7/2018 | Giladi et al. |
| 2019/0117956 A1 | 4/2019 | Wenger et al. |
| 2019/0307781 A1 | 10/2019 | Krex et al. |
| 2019/0308016 A1 | 10/2019 | Wenger et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0023179 A1 | 1/2020 | Bomzon et al. |
| 2020/0061360 A1 | 2/2020 | Hagemann et al. |
| 2020/0061361 A1 | 2/2020 | Hagemann et al. |
| 2020/0069937 A1 | 3/2020 | Naveh et al. |
| 2020/0078582 A1 | 3/2020 | Alon et al. |
| 2020/0108031 A1 | 4/2020 | Borst et al. |

OTHER PUBLICATIONS

Communication Pursuant to Article 94(3) dated Mar. 18, 2022 by the EP Patent Office for EP Application No. 19772831.4 which was filed on Mar. 22, 2021 and (Inventor—Noa Kaynan et al.) (4 pages).

U.S. Appl. No. 62/695,925, filed Jul. 10, 2018, Noa Kayman (Novocure GmbH).

EP, 19772831.4, Jan. 16, 2020, Noa Kayman (Novocure GmbH).

PCT, PCT/IB2019/055852 (WO 220012364), Jul. 9, 2019 (Dec. 18, 2014), Noa Kayman (Novocure GmbH).

* cited by examiner

INHIBITING VIRAL INFECTION USING ALTERNATING ELECTRIC FIELDS

CROSS REFERENCE TO RELATED APPLICATIONS

This application claims the benefit of U.S. Provisional Application 62/695,925, filed Jul. 10, 2018, which is incorporated herein by reference in its entirety.

BACKGROUND

Viruses are small intracellular obligate parasites. Viruses include a nucleic acid that contains the genetic information necessary to program the synthetic machinery of the host cell for viral replication, and, in the simplest viruses, a protective protein coat.

To infect a cell, the virus must attach to the cell surface, penetrate into the cell, and become sufficiently uncoated to make its genome accessible to viral or host machinery for transcription or translation. Viruses' multiplication usually causes cell damage or death. Productive infection results in the formation of progeny viruses.

It has previously been shown that when cells are exposed to an alternating electric field (AEF) in specific frequency ranges while the cell is undergoing mitosis, the AEF can disrupt the mitosis process and cause apoptosis. This phenomenon has been successfully used to treat tumors (e.g. glioblastoma, mesothelioma, etc.) as described in U.S. Pat. Nos. 7,016,725 and 7,565,205, each of which is incorporated herein by reference in its entirety. And in the context of treating tumors, these alternating electric fields are referred to as "TTFields" (or "Tumor Treating Fields"). One of the reasons why TTFields therapy is well-suited for treating tumors is that TTFields selectively disrupt dividing cells during mitosis, and apparently have no effect on cells that are not dividing. And because tumor cells divide much more often than other cells in a person's body, applying TTFields to a subject will selectively attack the tumor cells while leaving the other cells unharmed. The same phenomenon has also been successfully shown to be useful for destroying bacteria, as described in U.S. Pat. No. 9,750,934, which is incorporated herein by reference in its entirety. And here again, one of the reasons why this approach is well-suited for destroying bacteria is that bacteria cells divide much more rapidly than other cells in a person's body.

SUMMARY OF THE INVENTION

One aspect of the invention is directed to a first method of inhibiting a virus from infecting cells in a target region. The first method comprises the steps of imposing an alternating electric field in the target region for a duration of time, the alternating electric field having a frequency and a field strength, wherein when the alternating electric field is imposed in the target region for the duration of time, the alternating electric field inhibits infection of the cells in the target region by the virus.

In some instances of the first method, the target region is a region within a live subject, and the alternating electric field is safe for the subject. In some of these instances, the target region is tumor-free.

In some instances of the first method, the target region is a region within a live subject, the alternating electric field is safe for the subject, and the first method further comprises the step of delivering an antiviral agent to the target region so that a therapeutically effective dose of the antiviral agent is present in the target region while the imposing is performed.

Some instances of the first method further comprise the step of delivering an antiviral agent to the target region so that the antiviral agent is present in the target region while the imposing is performed.

In some instances of the first method, the alternating electric field has a frequency between 50 and 500 kHz. In some instances of the first method, the alternating electric field has a frequency between 25 kHz and 1 MHz. In some instances of the first method, the alternating electric field has a frequency of about 200 kHz.

In some instances of the first method, the alternating electric field has a field strength between 1 and 5 V/cm RMS. In some instances of the first method, the alternating electric field has a field strength of about 1.2 V/cm RMS.

In some instances of the first method, the duration of time is between 1 and 48 hours. In some instances of the first method, the duration of time is between 2 and 14 days. In some instances of the first method, the duration of time is about 48 hours.

In some instances of the first method, the alternating electric field has an orientation that is repeatedly switched between at least two directions during the duration of time. In some of these instances, the orientation of the alternating electric field is switched about once a second.

In some instances of the first method, the alternating electric field has an orientation that is repeatedly switched between a first direction and a second direction during the duration of time, and the first direction is roughly perpendicular to the second direction.

In some instances of the first method, the alternating electric field is applied to the target region via capacitively coupled electrodes.

BRIEF DESCRIPTION OF THE DRAWINGS

Various embodiments are described in detail below with reference to the accompanying drawings, wherein like reference numerals represent like elements.

DETAILED DESCRIPTION OF THE PREFERRED EMBODIMENTS

Surprisingly, the inventors have shown that alternating electric fields can also be used to inhibit viral infections. These results are surprising because AEF operates in the contexts described above by disrupting dividing cells during mitosis. But unlike tumor cells and bacteria, viruses do not replicate by mitosis.

Two in vitro experiments establishing that AEFs can inhibit viral infection will now be described. These experiments used a Novocure™ Inovitro™ test setup to measure Lentiviral infection of human embryonic kidney HEK293FT cells obtained from ThermoFisher Scientific.

Figure 1:
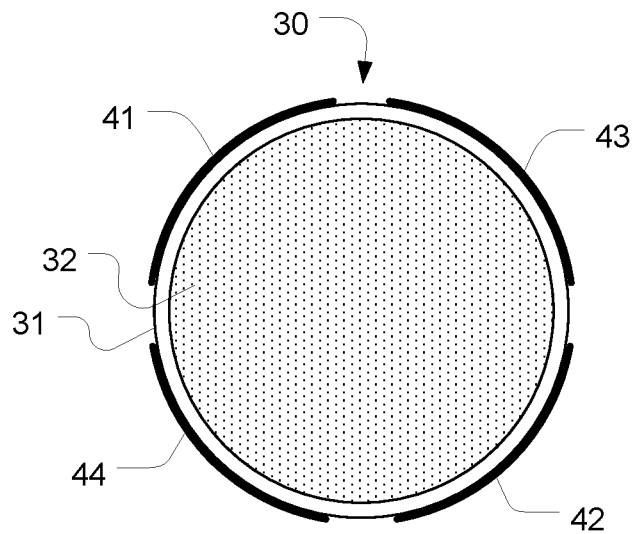
FIG. 1 is a schematic representation of a dish that was used for two in vitro experiments.

The Inovitro™ test setup includes eight dish-shaped containers, each of which is shaped and dimensioned for holding a culture, and FIG. 1 is a schematic representation of a representative one of these dishes. Each dish 30 includes ceramic sidewalls 31 and a bottom panel 32 that, taken together, form the dish. A plurality of electrodes 41-44 is disposed on the outer surface of the ceramic sidewalls 31 at positions selected so that when a culture is positioned in the container, application of a voltage between the plurality of electrodes 41-44 induces an electric field through the culture. More specifically, (a) application of an AC voltage between electrodes 41 and 42 induces an alternating electric field in a first direction through the culture, and (b) application of an AC voltage between electrodes 43 and 44 induces an alternating electric field in a second direction through the culture. In the FIG. 1 embodiment, the second direction is perpendicular to the first direction due to the placement of the electrodes 41-44 on the ceramic sidewalls 31. Note that if one subset of electrodes (e.g. electrodes 41 and 42) were to be shifted by a small angle (e.g. less than 10°), the second direction would be roughly perpendicular to the first direction.

Figure 2:
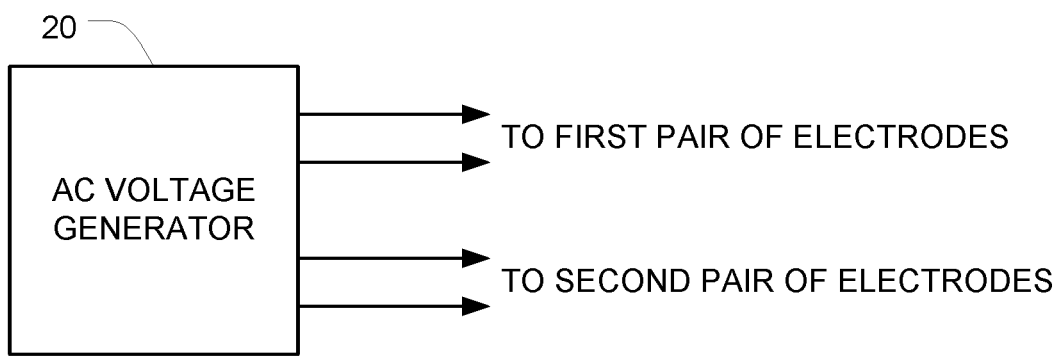
FIG. 2 is a schematic representation of an AC voltage generator that is used to apply AC voltages to the electrodes in the various embodiments described herein.

Turning now to FIG. 2, an AC voltage generator 20 generates signals that are applied to the first pair of electrodes 41, 42 and the second pair of electrodes 43, 44. The AC voltage generator 20 applies an AC voltage at a selected frequency between the first pair of electrodes 41, 42 for one second, then applies an AC voltage at the same frequency between the second pair of electrodes 43, 44 for one second, and repeats this two step sequence for the duration of the experiment. The system also includes thermal sensors (not shown), and the AC voltage generator 20 will decrease the amplitude of the AC voltages that are being applied to the electrodes if the sensed temperature of the dish 30 gets too high.

Figure 3:
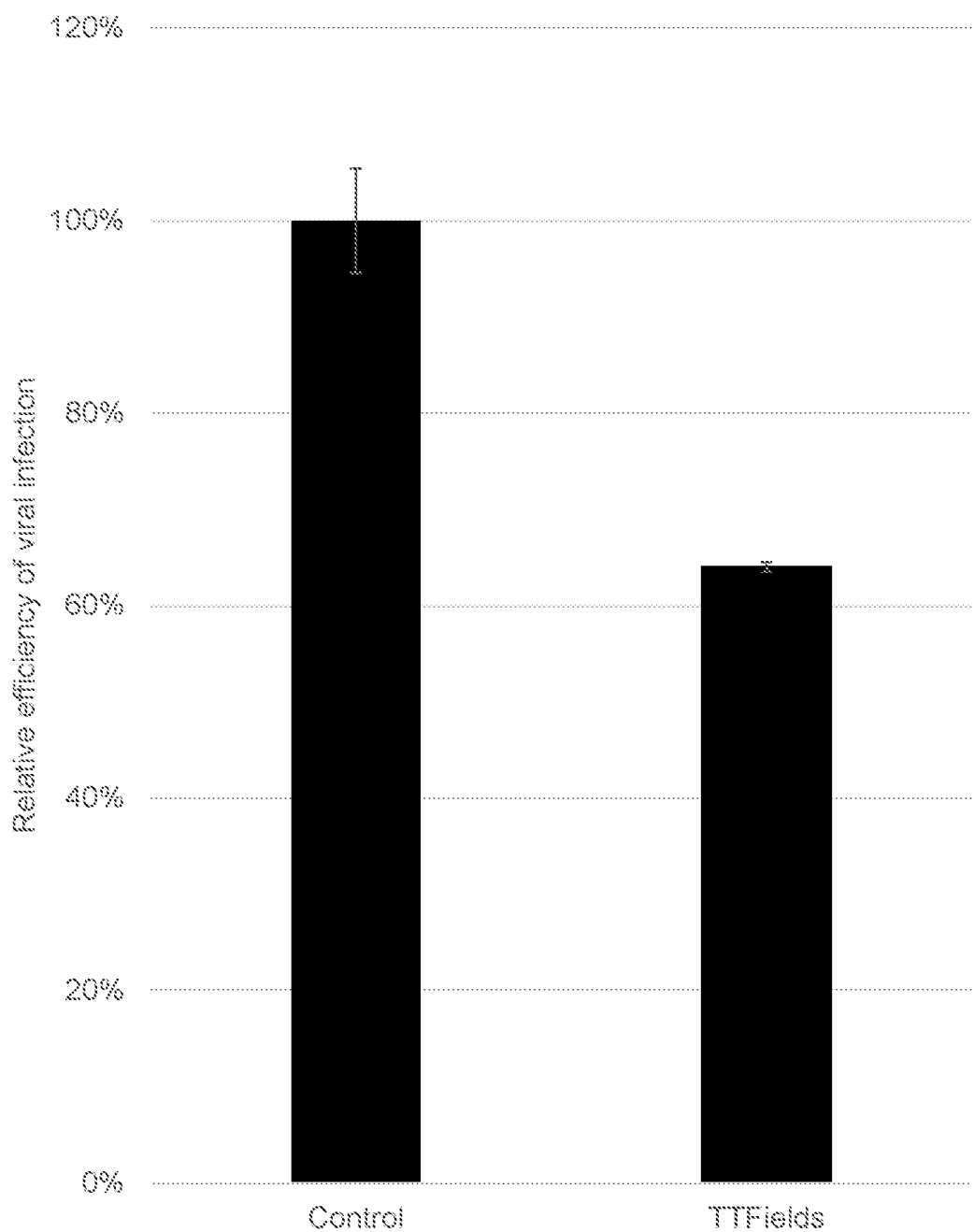
FIG. 3 depicts the relative infection efficiency with respect to the control for a first experiment.

In the first experiment, the kidney cells were exposed to a lentivirus that encodes for a Green Fluorescent Protein (GFP). For this experiment, a Dharmacon™ Trans-Lentiviral Packaging Kit with Calcium Phosphate Transfection Reagent TLP5916 and Precision LentiORF RFP Control DNA OHS5832 were used. The Multiplicity of Infection was 5, and 200 kHz AEFs with a field strength of 1.2 V/cm RMS were applied to the culture for 48 hours. The direction of the AEFs was switched every second as described above. A control was subjected to the exact same conditions except that the AEFs were not applied. At the end of the 48 hour period, infected cells were identified based on the presence of GFP (i.e., the presence of GFP means that the cell was infected). Infection efficiency was measured by flow cytometry analysis as the % of cells expressing the viral-encoded GFP. The percentage of infected cells in the AEF treated culture was 30%; and the percentage of infected cells in the control culture was 47%. Relative infection efficiency (with respect to the control) was then calculated. The results, which are depicted in FIG. 3, were as follows: for the 200 kHz AEFs, the relative infection level was 64±0.5% as compared to the control cells (100±5.4%, $p<0.01$, student T test).

At the end of the 48 hour period, observation revealed that the cells were dividing during the course of the experiment for both the AEF treated cultures and the control; and that there was no significant effect on the total number of cells as between the AEF treated cultures and the control. One possible explanation for this may be the relatively short (48 hour) treatment duration combined with the low field intensity that was used, since the AEFs could be applied in no less than 27° C.

Figure 4:
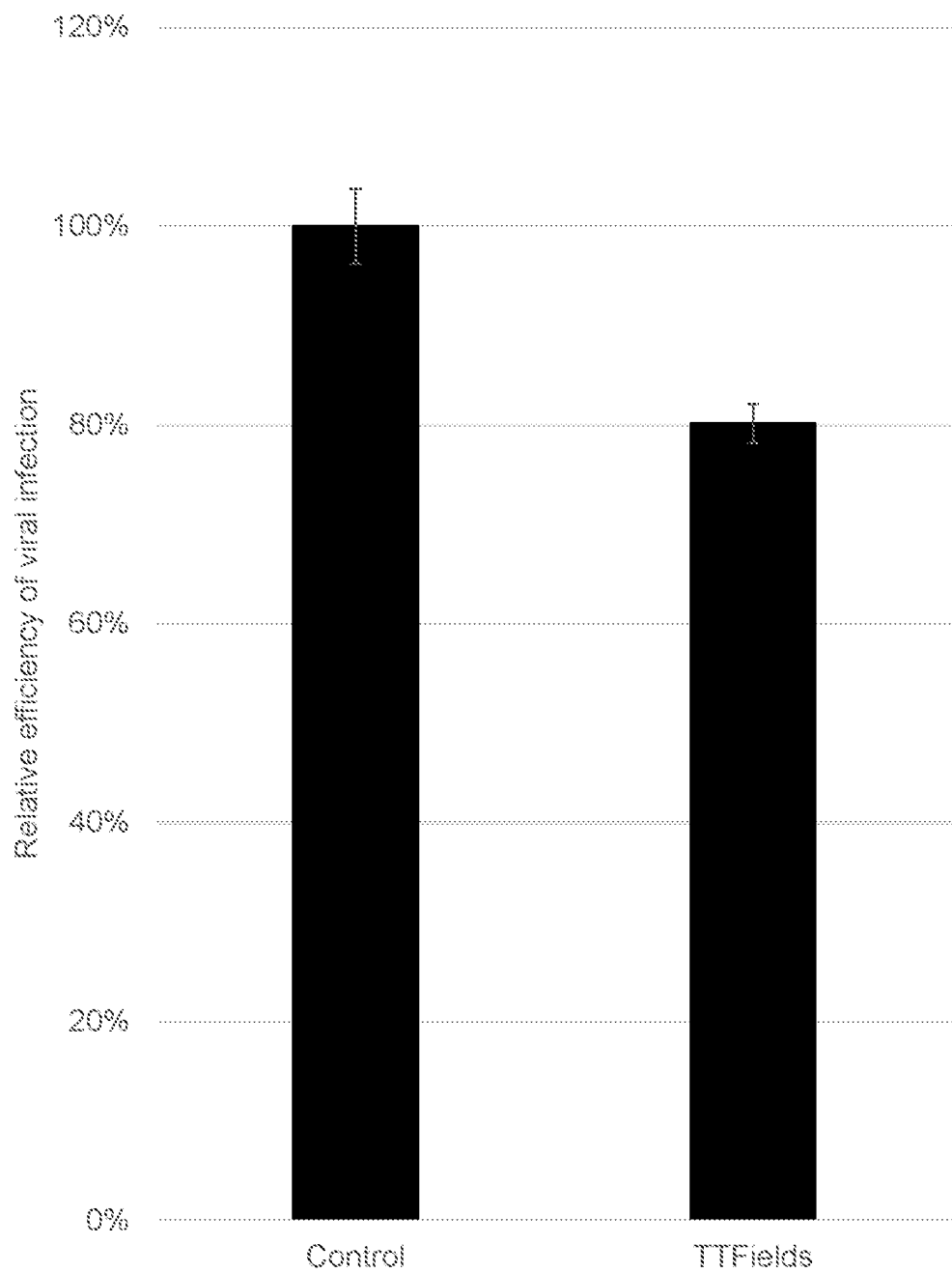
FIG. 4 depicts the relative infection efficiency with respect to the control for a second experiment.

The second in vitro experiment was identical to the first experiments in all respects except that a 100 kHz AEF was used in place of the 200 kHz AEF that was used in the first experiment. The results of this second experiment were as follows: The percentage of infected cells in the AEF treated culture was 51%; and the percentage of infected cells in the control culture was 64%. Relative infection efficiency (with respect to the control) was then calculated. The results, which are depicted in FIG. 4, were as follows: for the 100 kHz AEFs, the relative infection level was 80±2% as compared to the control cells (100±3.7%, $p<0.01$ $p<0.0005$, student T test).

In the two in vitro experiments described above, the frequency of the AEFs was either 100 or 200 kHz. But in alternative embodiments, the frequency of the AEFs could be another frequency between 50 and 500 kHz. In other embodiments, the frequency of the AEFs could be between 25 kHz and 1 MHz. In other embodiments, the frequency of the AEFs could be between 1 and 10 MHz. In still other embodiments, the frequency of the AEFs could be between 10 and 100 MHz. The optimal frequency may be determined experimentally for each combination of a given type of host cell and a given type of virus that is either infecting or attempting to infect the host cells, depending on the intended use. Preferably, care is taken to ensure that the frequency selected does not adversely heat the target region.

In the two in vitro experiments described above, the field strength of the AEFs was 1.2 V/cm RMS. But in alternative embodiments, a different field strength may be used (e.g., between 0.2 and 1 V/cm RMS, between 1 and 5 V/cm RMS, or between 5 and 25 V/cm RMS. The optimal field strength may be determined experimentally for each combination of a given type of host cell and a given type of virus that is either infecting or attempting to infect the host cells, depending on the intended use.

In the two in vitro experiments described above, the AEFs were applied for 48 hours. But in alternative embodiments, a different duration may be used (e.g., between 1 and 48 hours, or between 2 and 14 days). In some embodiments, application of the AEFs may be repeated periodically. For example, the AEFs may be applied every day for a two hour duration.

In the two in vitro experiments described above, the direction of the AEFs was switched at one second intervals between two perpendicular directions. But in alternative embodiments, the direction of the AEFs can be switched at a faster rate (e.g., at intervals between 1 and 1000 ms) or at a slower rate (e.g., at intervals between 1 and 100 seconds).

In the two in vitro experiments described above, the direction of the AEFs was switched between two perpendicular directions by applying an AC voltage to two pairs of electrodes that are disposed 90° apart from each other in 2D space in an alternating sequence. But in alternative embodiments the direction of the AEF may be switched between two directions that are not perpendicular by repositioning the pairs of electrodes, or between three or more directions (assuming that additional pairs of electrodes are provided). For example, the direction of the AEFs may be switched between three directions, each of which is determined by the placement of its own pair of electrodes. Optionally, these three pairs of electrodes may be positioned so that the resulting fields are disposed 90° apart from each other in 3D space. In other alternative embodiments, the electrodes need not be arranged in pairs. See, for example, the electrode positioning described in U.S. Pat. No. 7,565,205, which is incorporated herein by reference. In other alternative embodiments, the direction of the field need not be switched at all, in which case the second pair of electrodes 43, 44 (shown in FIG. 1) can be omitted.

In the two in vitro experiments described above, the electrical field was capacitively coupled into the culture because the conductive electrodes 41-44 were disposed on the outer surface of the ceramic sidewalls 31, and the ceramic material of the sidewalls 31 acts as a dielectric. But in alternative embodiments, the electric field could be applied directly to the culture without capacitive coupling (e.g., by modifying the configuration depicted in FIG. 1 so that the conductive electrodes are disposed on the sidewall's inner surface instead of on the sidewall's outer surface).

In the two in vitro experiments described above, human embryonic kidney HEK293FT cells were positioned in a target region within a dish 30 (shown in FIG. 1), and a lentivirus was used to infect those cells. Imposing the alternating electric field in the target region inhibited infection of the cells in the target region by the virus. In alternative embodiments, different cell types and/or different virus types may be used.

Figure 5A:
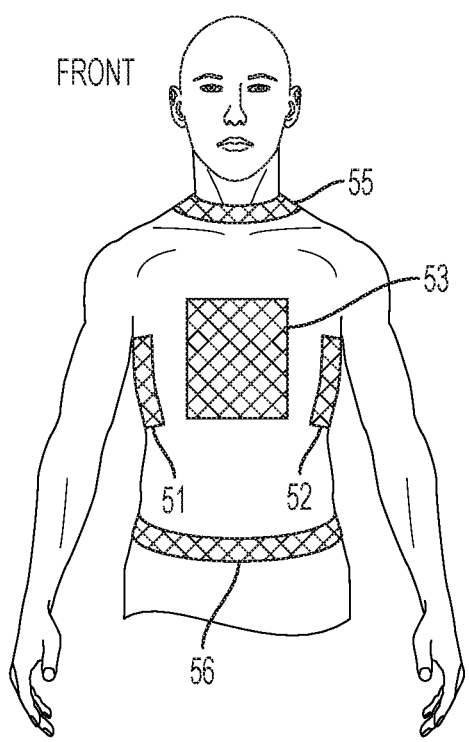
FIGS. 5A and 5B depict front and back views, respectively, for positioning electrodes on a subject's body in an exemplary embodiment.
Figure 5B:
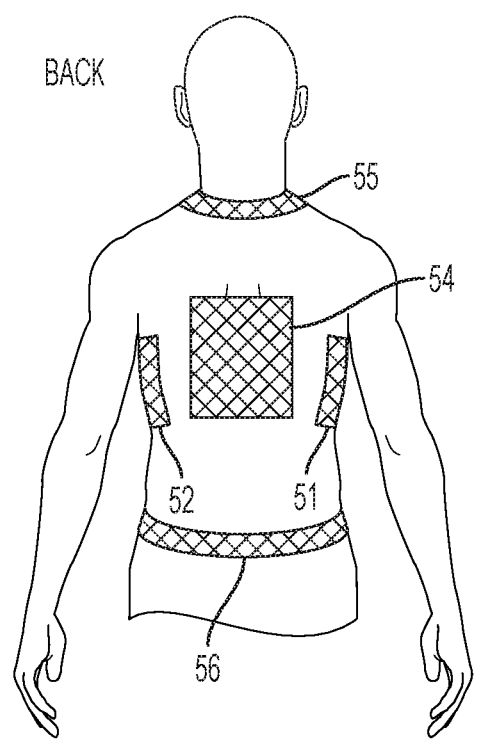

These results can be applied to the in vivo context by applying the AEFs to a target region of a live subject's body. Imposing the alternating electric field in the target region will inhibit infection of the cells in the target region by the virus. This may be accomplished, for example, by positioning electrodes on the subject's skin or subcutaneously so that application of an AC voltage between selected subsets of those electrodes will impose the AEF in the target region of the subject's body. For example, in situations where the virus at issue typically colonizes the lungs, the electrodes 51-54 could be positioned as depicted in FIGS. 5A and 5B. In some embodiments, the electrodes are capacitively coupled to the subject's body (e.g., by using electrodes that include a conductive plate and also have a dielectric layer disposed between the conductive plate and the subject's body). But in alternative embodiments, the dielectric layer may be omitted, in which case the conductive plates would make direct contact with the subject's body.

The AC voltage generator 20 (shown in FIG. 2) applies an AC voltage at a selected frequency (e.g. 200 kHz) between the first pair of electrodes 51, 52 for a first period of time (e.g. 1 second), which induces an AEF where the most significant components of the field lines are parallel to the transverse axis of the subject's body. Then, the AC voltage generator 20 applies an AC voltage at the same frequency (or a different frequency) between the second pair of electrodes 53, 54 for a second period of time (e.g. 1 second), which induces an AEF where the most significant components of the field lines are parallel to the sagittal axis of the subject's body. This two step sequence is then repeated for the duration of the treatment. Optionally, thermal sensors (not shown) may be included at the electrodes, and the AC voltage generator 20 can be configured to decrease the amplitude of the AC voltages that are applied to the electrodes if the sensed temperature at the electrodes gets too high. In some embodiments, one or more additional pairs of electrodes may be added and included in the sequence. For example, when the additional pair of electrodes 55, 56 shown in FIGS. 5A and 5B are added, and the AC voltage generator 20 applies an AC voltage to those electrodes, it would induce an AEF where the most significant components of the field lines are parallel to the longitudinal axis of the subject's body. Note that any of the parameters for this in vivo embodiment (e.g., frequency, field strength, duration, direction-switching rate, and the placement of the electrodes) may be varied as described above in connection with the in the vitro embodiment. But care must be taken to ensure that the alternating electric field remains safe for the subject at all times.

In the in vivo context, the AEFs may be applied to a target region (e.g., the lungs of a first person) that is tumor free. Alternatively, the AEFs may be applied to a target region that contains a tumor (e.g., the lungs of a different person).

In any of the embodiments described above, the application of AEFs may be combined with delivering an antiviral agent to the target region so that a therapeutically effective dose of the antiviral agent is present in the target region while the imposing of the AEF is performed.

Because AEFs can inhibit viral infection, applying AEFs can prevent the damage made by infection of new cells (alteration of cell's functions, cell death or transformation), stop viral multiplication and spread, and avoid its ramifications on the wellbeing of the infected person.

AEF-based anti-viral therapy may also be used for the protection of uninfected healthy individuals from a threatening infection, like in the case of medical staff that come into close contact with infected individuals (especially in acute phases of viral diseases when infectious particles may be found in blood, skin lesions, saliva etc., and can be transmitted by direct or indirect contact, e.g., via droplets or aerosols).

AEF-based anti-viral protection may also be used by individuals with suppressed immune system (like in cases of congenital immunodeficiency, organ transplant, cancer etc.), which lack the natural forceful defense of the body, hence are extremely sensitive to opportunistic infections.

Additionally, inhibition of viral infection could be of enormous importance to the progression of an ongoing viral disease. Human immunodeficiency virus (HIV) is an example for a virus that remains clinically dormant in the human body for a long period of time, however, during this period the virus persists and replicates, particularly in lymph nodes. Over time the number of the susceptible immune cells decline following infection and AIDS (Acquired Immune Deficiency Syndrome) develops. Halting the continuous cycles of viral infection would seize the spread within and prevent the progression of the disease.

Furthermore, AEF-based anti-viral therapy could potentially show even higher effect if combined with additional anti-viral drugs.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of inhibiting a virus from infecting cells in a target region, comprising the steps of:

imposing an alternating electric field in the target region for a duration of time, the alternating electric field having a frequency and a field strength, wherein when the alternating electric field is imposed in the target region for the duration of time, the alternating electric field inhibits infection of the cells in the target region by the virus, wherein the target region is tumor-free.

2. The method of claim 1, wherein the target region is a region within a live subject, and wherein the alternating electric field is safe for the subject.

3. The method of claim 2, further comprising a step of delivering an antiviral agent to the target region so that a therapeutically effective dose of the antiviral agent is present in the target region while the imposing is performed.

4. The method of claim 1, further comprising the step of delivering an antiviral agent to the target region so that the antiviral agent is present in the target region while the imposing is performed.

5. The method of claim 1, wherein the alternating electric field has a frequency between 50 and 500 kHz.

6. The method of claim 1, wherein the alternating electric field has a frequency between 25 kHz and 1 MHz.

7. The method of claim 1, wherein the alternating electric field has a frequency of about 200 kHz.

8. The method of claim 1, wherein the alternating electric field has a field strength between 1 and 5 V/cm RMS.

9. The method of claim 1, wherein the alternating electric field has a field strength of about 1.2 V/cm RMS.

10. The method of claim 1, wherein the duration of time is between 1 and 48 hours.

11. The method of claim 1, wherein the duration of time is between 2 and 14 days.

12. The method of claim 1, wherein the duration of time is about 48 hours.

13. The method of claim 1, wherein the alternating electric field has an orientation that is repeatedly switched between at least two directions during the duration of time.

14. The method of claim 13, wherein the orientation of the alternating electric field is switched about once a second.

15. The method of claim 1, wherein the alternating electric field has an orientation that is repeatedly switched between a first direction and a second direction during the duration of time, wherein the first direction is roughly perpendicular to the second direction.

16. The method of claim 1, wherein the alternating electric field is applied to the target region via capacitively coupled electrodes.

\* \* \* \* \*